(12) United States Patent
Fournet et al.

(10) Patent No.: US 8,026,231 B2
(45) Date of Patent: Sep. 27, 2011

(54) AMINOTHIOLESTER COMPOUNDS, PHARMACEUTICAL AND COSMETIC COMPOSITIONS CONTAINING SAME AND USES THEREOF

(75) Inventors: Guy Fournet, Villeurbanne Cedex (FR); Gerard Anthony Quash, Crapone (FR); Jacques Gore, Lyons (FR)

(73) Assignee: CNRS, Paris (FR)

( * ) Notice: Subject to any disclaimer, the term of this patent is extended or adjusted under 35 U.S.C. 154(b) by 1164 days.

(21) Appl. No.: 11/390,480

(22) Filed: Mar. 28, 2006

(65) Prior Publication Data

US 2007/0032476 A1 Feb. 8, 2007

Related U.S. Application Data

(63) Continuation of application No. 10/296,927, filed as application No. PCT/FR01/01694 on May 31, 2001, now Pat. No. 7,078,402.

(30) Foreign Application Priority Data

May 31, 2000 (FR) ...................................... 00 07029

(51) Int. Cl.
- *A61K 31/33* (2006.01)
- *A61K 31/535* (2006.01)
- *A01N 37/00* (2006.01)
- *C07D 279/10* (2006.01)
- *C07D 265/30* (2006.01)
- *C07D 295/00* (2006.01)
- *C07C 327/00* (2006.01)

(52) U.S. Cl. ...................... 514/183; 514/238.8; 514/513; 544/56; 544/158; 544/399; 548/572; 558/252

(58) Field of Classification Search ........................ None
See application file for complete search history.

(56) References Cited

U.S. PATENT DOCUMENTS

| 5,051,528 A | 9/1991 | Naujokas et al. |
| 6,028,114 A | 2/2000 | Quash |
| 6,117,902 A | 9/2000 | Quash et al. |
| 6,580,005 B1 | 6/2003 | Yazaki et al. |

FOREIGN PATENT DOCUMENTS

| EP | 0947503 A1 | 10/1999 |
| EP | 1 227 075 A1 | 7/2002 |
| EP | 0 973 715 B1 | 8/2002 |
| WO | 98/44919 A1 | 10/1998 |

OTHER PUBLICATIONS

Definition of inhibition. www.freedictionary.com. 2009.*
Definition of prohibiting. www.freedictionary.com. 2009.*
Blatt. Prostate cancer—Deciding what to do. Rome Sentinel Prime Time. 2005.*
Freshney. Culture of Animal Cells. A manual of basic technique, Alan R. Liss, 1983, New York. p. 4.*

Dermer (Bio/Technology, 1994, 12:320).*
Gura (Science, v278, 1997, pp. 1041-1042).*
Quash et al., "Novel competitive irreversible inhibitors of aldehyde dehydrogenase (ALDH1): restoration of chemosensitivity of L1210 cells overexpressing ALDH1 and induction of apoptosis in $BAF_3$ cells overexpressing $bcl_2$", Biochemical Pharmacology 64, pp. 1279-1292, 2002, Elsevier Science, England.
Miyashita et al., "Bcl-2 Oncoprotein Blocks Chemotherapy-Induced Apoptosis in a Human Leukemia Cell Line", Blood, vol. 81, No. 1, pp. 151-157, 1993, The American Society of Hematology, US.
Monneuse et al., "Intraperitoneal Treatment with Dimethylthioampal (DIMATE) Combined With Surgical Debulking Is Effective for Experimental Peritoneal Carcinomatosis in a Rat Model," *J. Gastrointestinal Surgery*, vol. 9, No. 6 pp. 769-774, (2005) Elsevier Inc.
Quash et al., "Aldehyde dehydrogenase inhibitors: $\alpha$, $\beta$-Acetylenic N-substituted aminothiolesters are reversible growth inhibitors of normal epithelial but irreversible apoptogens for cancer epithelial cells from human prostate in culture," *European Journal of Medicinal Chemistry*, 43, (2008) pp. 906-916, Elsevier Masson SAS.
Hiltbrand et al., "Synergetic Bitherapy in Mice with Xenografts of Human Prostate Cancer Using a Methional Mimic (METLICO) and an Adehyde Dehydrogenase 3 Inhibitor (MATE): Systemic Intraperiotoneal (IP) and Targeted Intra-tumoral (IT) Administration," *Current Medicinal Chemistry*, (2009), vol. 16, No. 10, pp. 1184-1191, Bentham Science Publishers, Ltd.
Backlund, P.S.; Chang, C.P.; Smith, R.A. *J. Biol. Chem.* (1982) 257:4196-4202.
Canuto, R.A.; Muzio, G; Salvo, R.A.; Maggiora, M.: Trombetta, A.; Chantepie, J.: Fournet, G.; Reichert, U.; Quash, G. *Chem-Biol. Interact.*, (2001) 130-132, 209-218.
Chen, D., Cui, Q.C.; Yang, H. And Ping Dou, Q. *Cancer. Res.* (2006) 66:10425-10433.
Furuya, Y.; Krajewski, S.; Epstein, J.I.; Reed, J.C. *Clin. Cancer Res.*, (1996) 2:389-98.

(Continued)

*Primary Examiner* — Brandon Fetterolf
*Assistant Examiner* — Anna Pagonakis
(74) *Attorney, Agent, or Firm* — Buchanan Ingersoll & Rooney PC

(57) ABSTRACT

The invention relates to novel aminothiol ester compounds having the general formula (I):

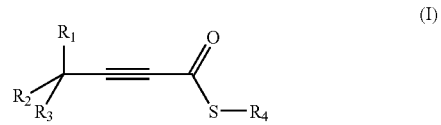

(I)

and to a method for preparing them and to their use in pharmaceutical compositions intended for use in human or veterinary medicine (cancers and precancers, dermatological, rheumatic and ophthalmological complaints in particular) or in cosmetic compositions.

The invention also relates to a pharmaceutical or cosmetic composition, characterized in that it comprises, as active agent, a compound of general formula (I) in combination with a pharmaceutically or cosmetically acceptable support.

7 Claims, 3 Drawing Sheets

OTHER PUBLICATIONS

Haynes, R.L.; Szweda, L.; Pickin, K.; Welker, M.E.; Townsend, A.J. *Mol. Pharmacol.*, (2000) 58:788-794.

Li, L.; Hamilton, R.F.; Kirichenko, A.; Holian, A. *Toxicol. Appl. Pharmacol.*, (1996) 139:135-143.

McDonnell, T.J.; Troncoso, P. and Brisbay, S.M.; Logothetis, C.; Chung, L.W.; Hsieh, J.T.; Tu, S.M. and Campbell, M.L. *Cancer Res.* (1992) 52:6940-6944.

Melino, G.; Knight, R.; Green, D. *Cell Death Differ.* (2001) 8:1-3.

Murphy, F.; Seery, L.; Hayes, I. in Essays in Biochemistry, Cotter. T.G. Ed., Portland Press, London (2003) vol. 39, pp. 131-153.

Miyashita, T.; Reed J.C. *Blood* (1993) 81:151-7.

Ogier, G.; Chantepie, J.; Deshayes C.; Chantegrel B.; Chariot C.; Doutheau A.; Quash G. *Biochem. Pharmacol.* (1993) 45:1631-1644.

Quash, G.; Fornet, G.; Raffin, C.; Chantepie, J.; Michal, Y.; Gore, J.; Reichert, U. *Adv. Exp. Med. Biol.* (1999) 7:97-106.

Quash, G.; Roch, A.M.; Chantepie J.; Michal Y.; Fournet G.; Dumontet C. *Biochem. J.* (1995) 305:1017-25.

Quash, G.; Fournet, G.; Courvoisier, C.; Martinez, M.; Chantepie, J.; Paret, J.; Pharaboz, J.; JolyPharaboz, M.O.; Gore J.; Andre, J.; Reichert U. *Eur. J. Med. Chem.* (2008) 43:906-916.

Quash, G.; Fournet, G.; Chantepie, J.; Ardiet, C.; Ardail, D.; Michal, Y.; Gore, J.; Reichert, U. *Biochemical Pharmacol.* (2002) 64:1279-1292.

Roch, A.M.; Quash, G.; Michal, Y.; Chantepie, J.; Chantegrel, B.; Deshayes, C.; Doutheau, A.; Marvel, J. *Biochem. J* (1996) 313:973-81.

Summerfield, F.W.; Tappel, A.L. *Chem. Biol. Interact.* (1984) 50:87-96.

Tang, B.; Kadariya, Y.; Murphy, M.E.; Kruger, W. *Biochem. Pharmacol.* (2006) 72:806-815.

Townsend, A.J.; Leone-Kabler, S.; Haynes, R.L.; Wu, Y.; Szweda, L.; Bunting, K.D. *Chem Biol Interact* (2001) 130-132, 261-273.

* cited by examiner

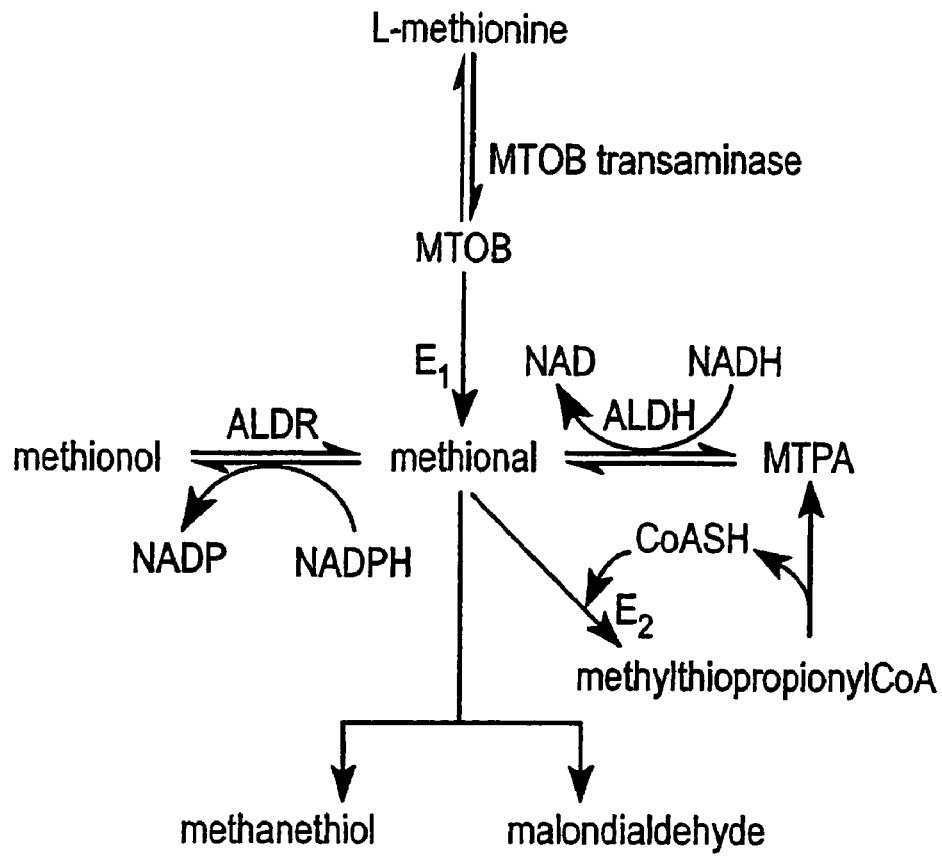

- MTOB represents 4-methylthio-2-oxobutanoic acid,
- MTPA represents methylthiopropionic acid,
- $E_1$ represents the decarboxylase of the branched-chain oxo-acid dehyrogenase complex whose co-factor is thiamine pyrophosphate,
- $E_2$ represents the transacylase of the branched-chain oxo-acid dehydrogenase complex whose co-factor is thioctic acid,
- ALDR represents aldehyde reductase,
- ALDH represents aldehyde dehydrogenase,
- CoASH represents acetyl coenzyme A,
- NADH/NAD represents nicotinamide adenine dinucleotide, and
- NADPH/NADP represents nicotinamide adenine dinucleotide phosphate.

FIG. 1

AMINOTHIOLESTER COMPOUNDS, PHARMACEUTICAL AND COSMETIC COMPOSITIONS CONTAINING SAME AND USES THEREOF

CROSS-REFERENCE TO RELATED APPLICATIONS

This is a continuation of application Ser. No. 10/296,927, filed May 6, 2003 now U.S. Pat No. 7,078,402, now allowed, incorporated by reference herein in its entirety and relied upon, which is the United States national phase of International Application No. PCT/FR01/01694, filed May 31, 2001 in France, claiming the priority of French Application No. 00/07029, filed May 31, 2000.

The present invention relates to aminothiol ester compounds of formula (I) and to their use as cell apoptosis inducers. The compounds according to the invention have pronounced activity as apoptosis inducers and find applications more particularly in the topical and systemic treatment of cancers and precancers and dermatological, rheumatic and ophthalmological complaints.

The present invention also relates to a pharmaceutical or cosmetic composition containing, as active agent, at least one aminothiol ester compound of formula (I) in a physiologically acceptable excipient.

The term "apoptosis" means the phenomenon of cell death as described, inter alia, by Kerr J. F. R. et al., J. Cancer, 265, 239 (1972). Apoptosis, which is a highly selective form of cell suicide, is characterized by readily observable morphological and biochemical phenomena. Thus, a condensation of chromatin possibly associated with an endonuclease activity, the formation of apoptotic bodies and a fragmentation of deoxyribonucleic acid (DNA), due to the activation of endonucleases, into DNA fragments of 180-200 base pairs, giving a profile which is readily recognizable by agarose gel electrophoresis, are thus observed.

Apoptosis is involved in tissue development, differentiation and renewal. Inducing apoptosis is thus of major interest from a therapeutic viewpoint, and also from a cosmetic viewpoint.

A very large variety of natural or synthetic anticancer medicinal products currently available are apoptosis-inducing compounds.

Among these antineoplastic medicinal products, mention may be made of alkylating agents such as cyclophosphamide, nitrosureas such as 1,3-bis(2-chloroethyl)-1-nitrosourea (BCNU), intercalating agents such as actinomycin D or adriamycin, purine or pyrimidine base analogues such as 6-thioguanine and 5-fluorouracil, inhibitors of the de novo synthesis of purine bases, such as methotrexate, and finally tubulin polymerization inhibitors such as Taxol®.

Moreover, it has already been proposed by the Applicant, in particular in patent application WO 96/20701, to use an apoptosis-inducing compound chosen from methional, malonaldehyde and any factor for increasing the intracellular level of these compounds, that is to say any compound having an action on the metabolism of methional, which is shown as a reminder in FIG. 1 (Quash et al., Biochem. J. 305, 1017 (1995)).

4-Methylthio-2-oxobutanoic acid (MTOB) transaminase inhibitors, composed of esters of L-methionine and of pyridoxal, have also been disclosed in the said patent application, as factors for increasing the intracellular level of methional. As MTOB transaminase is an enzyme involved in the conversion of 4-methylthio-2-oxobutanoic acid to methionine, the use of these compounds promotes the accumulation of MTOB, a direct precursor of methional (FIG. 1) (Roch et al., Biochem. J. 313, 973 (1996)).

One of the main drawbacks in using these substances is the absence of selective apoptotic activity on tumour cells. Thus, it remains necessary to have available molecules which induce maximum apoptosis in tumour tissue while causing the least possible injury, and in a reversible manner, to the healthy tissues of the body.

In order to overcome this absence of selectivity, the Applicant has disclosed, in patent application WO 98/44919, the use of aminothiol ester derivatives, including thioampal, as inhibitors of the enzyme aldehyde dehydrogenase (ALDH), an enzyme involved in the conversion of methional to methylpropionic acid, thus promoting the accumulation of methional. These compounds are selective inhibitors of the growth of transformed cells that are apoptosis-resistant due to overexpression of the bcl$_2$ gene.

Such compounds are thus more specifically intended for treating pathologies characterized by an overexpression of the bcl$_2$ gene, such as breast cancer, B cell lymphoma, leukaemia, neuroblastoma, adenocarcinoma of the prostate, prolactinoma and other pituitary adenomas.

However, these aminothiol ester derivatives are difficult to prepare. Specifically, the processes for preparing them give a yield not exceeding 20%. Furthermore, these compounds have stability problems and must be stored at temperatures of about −20° C. to prevent them from degrading.

It was thus desirable to develop novel compounds which are stable and easy to prepare in good yields and which selectively inhibit the growth of transformed cells that are apoptosis-resistant due to overexpression of the bcl$_2$ gene.

This object of the present invention relates to novel aminothiol ester compounds which may be represented by the general formula (I) below:

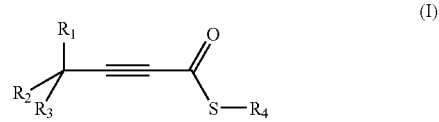

in which:

R$_1$ represents:

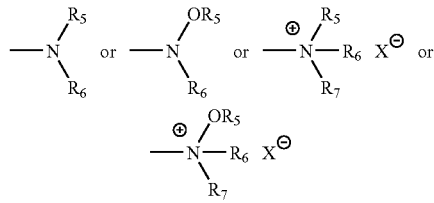

R$_2$ and R$_3$, independently, represent a saturated or unsaturated, cyclic, linear or branched alkyl radical containing from 1 to 7 carbon atoms or an aryl radical containing from 1 to 7 carbon atoms, or an aralkyl radical containing from 1 to 12 carbon atoms or, taken together, form a saturated alkyl ring containing from 3 to 7 carbon atoms, R$_4$ represents a saturated or unsaturated, cyclic, linear or branched alkyl radical containing from 1 to 7 carbon atoms or an aryl radical containing from 1 to 7 carbon atoms or an aralkyl radical containing from 1 to 12 carbon atoms, $R_5$ and $R_6$, independently, represent a saturated or unsaturated, cyclic, linear or branched alkyl radical containing from 1 to 7 carbon atoms or an aryl radical containing from 1 to 7 carbon atoms, or an aralkyl radical containing from 1 to 12 carbon atoms or, taken together, form, with the nitrogen atom, a saturated or unsaturated nitrogen heterocycle containing from 2 to 6 carbon atoms, optionally substituted with an oxygen, a sulphur or with a nitrogen atom optionally substituted with a saturated or unsaturated, cyclic, linear or branched alkyl radical containing from 1 to 7 carbon atoms or an aryl radical containing from 1 to 7 carbon atoms or an aralkyl radical containing from 1 to 12 carbon atoms, $R_7$ represents a hydrogen atom, a saturated or unsaturated, cyclic, linear or branched alkyl radical containing from 1 to 7 carbon atoms or an aryl radical containing from 1 to 7 carbon atoms or an aralkyl radical containing from 1 to 12 carbon atoms, and X represents a halide ion or a nitrate, sulphate, sulphonate, carboxylate, thiocyanate or phosphate anion.

Among the cyclic alkyl radicals containing from 3 to 7 carbon atoms, mention may be made in particular of cyclopropyl, cyclopentyl, cyclohexyl and cycloheptyl radicals.

Among the saturated linear alkyl radicals containing from 1 to 7 carbon atoms, mention may be made in particular of methyl, ethyl, n-propyl, n-butyl, n-pentyl, n-hexyl or n-heptyl radicals.

Among the saturated and branched alkyl radicals containing from 1 to 7 carbon atoms, mention may be made in particular of i-propyl, t-butyl, 2-butyl, 2-pentyl, i-pentyl, 2-hexyl, 3-hexyl, 2-heptyl, 3-heptyl or i-heptyl radicals.

Among the unsaturated alkyl radicals containing from 1 to 7 carbon atoms, mention may be made in particular of the allyl or vinyl radical.

The expression "aralkyl radical containing from 1 to 12 carbon atoms" means a phenyl radical optionally substituted with linear or branched alkyl radicals containing from 1 to 5 carbon atoms linked to a saturated linear alkyl chain containing from 1 to 5 carbon atoms, such as the benzyl radical optionally substituted with an alkyl radical containing from 1 to 5 carbon atoms, or 1-phenylethyl, 1-phenylpropyl, 1-phenylbutyl or 1-phenylpentyl radicals.

Among the aryl radicals containing from 1 to 7 carbon atoms, mention may be made in particular of phenyl, tolyl, chlorophenyl, nitrophenyl, methoxyphenyl, thiophene and furan radicals. Among the nitrogen heterocycles, mention may be made in particular of pyrrolidine, piperidine, morpholine, thiamorpholine, piperazine, homopiperazine or N-methylpiperazine. Among the halides which may be mentioned are the fluorides, chlorides, bromides and, in particular, iodides.

BRIEF DESCRIPTION OF THE DRAWINGS

FIG. 1 is a schematic illustrating the metabolism of methional.

Among the compounds of formula (I) falling within the context of the present invention, mention may be made in particular of the following:

No. Compounds
1—S-methyl 4-dimethylamino-4-methyl-2-pentynethioate
2—S-methyl 4-methyl-4-trimethylammonium-2-pentynethioate iodide
3—S-methyl 4-di-n-propylamino-4-methyl-2-pentynethioate
4—S-methyl 4-methyl-4-pyrrodin-1-yl-2-pentynethioate
5—S-methyl 4-methyl-4-morpholin-4-yl-2-pentynethioate According to the present invention, the compounds of formula (I) that are more particularly preferred are those for which at least one of the conditions below is respected:

$R_2$ and $R_3$ represent a methyl radical;
$R_4$ represents a methyl radical;
$R_5$ and $R_6$, independently, represent an alkyl radical containing from 1 to 3 carbon atoms or, taken together, form, with the nitrogen atom, a nitrogen heterocycle chosen from pyrrolidine, piperidine and morpholine;
$R_7$ represents a methyl radical or a hydrogen atom; and
X represents an iodide ion, a formate ion or a carboxylate ion.

A subject of the present invention is also processes for preparing the compounds of formula (I).

Figure 2:
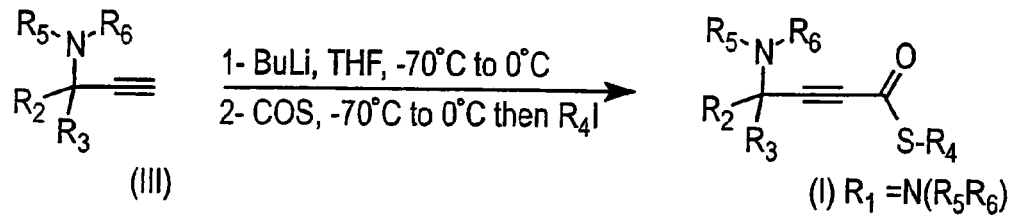
FIG. 2 is a reaction scheme depicting a method for the preparation of a compound of formula (I) in which $R_1$ is $NR_5R_6$ from a propargyl amine of formula (III).

The compounds of formula (I) ($R_1$=$N(R_5R_6)$) according to the invention may be obtained according to the reaction scheme shown in FIG. 2. The synthetic process consists in reacting butyllithium with a propargyl amine of formula (III) in THF. The intermediate lithium acetylene formed is reacted with carbon oxysulphide (COS) and then with the iodide $R_4I$. The thioester of formula (I) ($R_1$=$N(R_5R_6)$) is thus obtained in a yield of about 70%.

Figure 3:
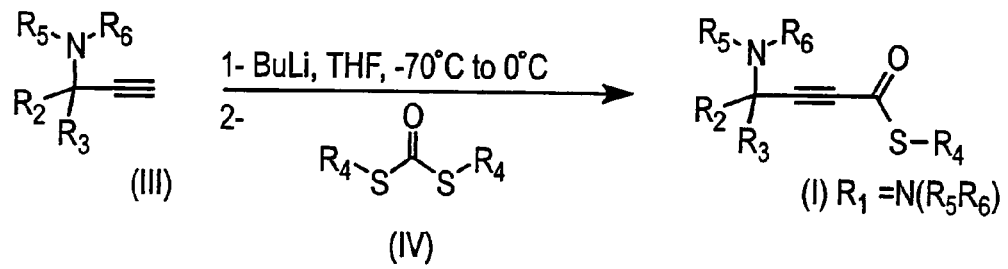
FIG. 3 is a reaction scheme depicting an alternate method for the preparation of a compound of formula (I) in which $R_1$ is $NR_5R_6$ from a propargyl amine of formula (III).

It may also be envisaged, as shown in FIG. 3, to react the lithium acetylene directly with a dialkyl or diaryl dithiocarbonate of formula (IV). These compounds are widely described, for example when $R_4$ represents a methyl radical [Douglass, I. B., Warner, G. H., 78, 6070-6071, (1956)].

Figure 4:
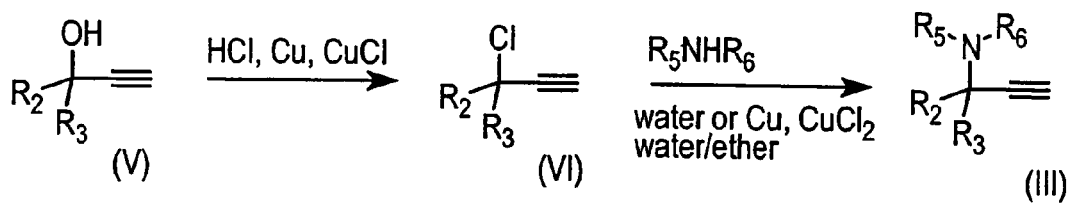
FIG. 4 is a reaction scheme depicting a method for the preparation of the propargyl amine starting material of formula (III).

The propargyl amines of formula (III) may be prepared according to the method of Hennion, G. F., Boiselle, A. P., J. Am. Chem. Soc., 26, 725-727, (1961). As shown in FIG. 4, this method consists in chlorinating the tertiary alcohol of formula (V) in hydrochloric acid medium in the presence of copper and cuprous chloride in a yield of about 70%.

The alcohol may be prepared, for example, from the ketone of formula $R_2COR_3$ and an acetylide.

The propargyl chloride of formula (VI) is then subjected to the action of the amine of formula $R_5NHR_6$ according to Hennion, G. F., Nelson, K. W., J. Am. Chem. Soc., 79, 2142-2144, (1957) and Hennion, G. F., Hanzel, R. F., J. Am. Chem. Soc., 82, 4908-4912, (1960). The yields generally obtained are between 20% and 60%.

Figure 5:
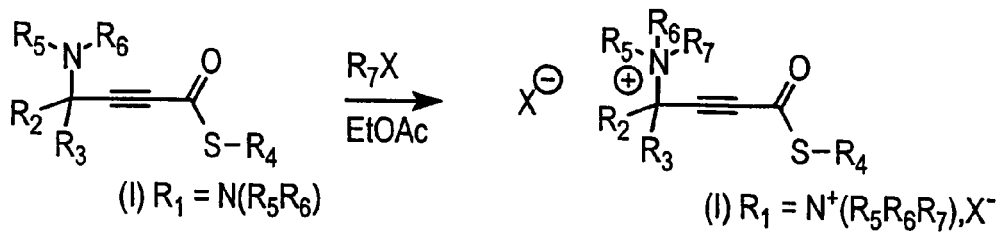
FIG. 5 is a reaction scheme depicting a method for the preparation of a compound of formula (I) in which $R_1$ is $N^+R_5R_6R_7X^-$ by reacting the halide $R_7X$ with a compound of formula (I) in which $R_1$ is $NR_5R_6$.

The compounds of formula (I) ($R_1=N^+(R_5R_6R_7)$, $X^-$) according to the invention may be synthesized according to the reaction scheme of FIG. 5. The synthetic process consists in reacting the halide $R_7X$ (preferably the iodide) or the mineral or organic acid ($R_7=H$) with the compound of formula (I) ($R_1=N(R_5R_6)$) The yields are about 70%.

Thus, whereas the synthesis of the compounds in patent application WO 98/44919 required a difficult step of deprotection of the propargyl amine which prevented these compounds from being prepared on a large scale, the synthesis of the compounds of the present invention has the advantage of being simpler and of being able to be developed on a large scale, in better yields.

These novel compounds also have the advantageous of being more stable and, especially, much more active in inhibiting the growth of transformed cells that are apoptosis-resistant due to overexpression of the $bcl_2$ gene than those disclosed in patent application WO 98/44919, such as thioampal.

The compounds according to the invention also have the advantage of being active in inhibiting the growth of transformed cells that are apoptosis-resistant not only due to overexpression of the $bcl_2$ gene, but also due to the expression of the ALDH enzymes (ALDH1, ALDH2 and/or ALDH3), overexpression of the MDR "Multi-Drug Resistant" gene or the BCL-$X_L$ gene, which broadens their field of use.

Thus, the present invention also relates to the use of at least one aminothiol ester derivative of formula (I) to prepare a pharmaceutical composition for removing the inhibition of a nature for resistance to the induction of apoptosis in transformed cells, this nature being due to the $bcl_2$ gene, the MDR gene or the BCL-$X_L$ gene present in these cells, or to the activity of ALDH.

The present invention also relates to the use of at least one aminothiol ester derivative of formula (I) to prepare a pharmaceutical composition for removing the inhibition of the chemotherapy-resistant or radiotherapy-resistant or the antiandrogen-resistant nature of transformed cells.

More particularly, the chemotherapy-resistant or antiandrogen-resistant nature of transformed cells is due to the $bcl_2$ gene, the BCL-$X_L$ gene or the MDR gene present in these cells or to the activity of the enzyme ALDH. More particularly, the radiotherapy-resistant nature of transformed cells is due to the presence of the $bcl_2$ gene or to the high level of glutathione in these cells.

Specifically, the aldehyde dehydrogenase (ALDH) enzymes catalyse the oxidation of various aliphatic and aromatic aldehydes to their corresponding carboxylic acid in the presence of the cofactor NAD or NADP. These enzymes of different sub-families, and in particular ALDH1, ALDH2 or ALDH3, are present in various organs and play a role in the detoxification of xenobiotics. Increasing the activity of these enzymes causes a resistance to anticancer agents such as cyclophosphamide [Magni et al., Blood, 87, 1097-1103, (1996)].

As indicated in patent application WO 98/44919, the use of an inhibitor of the activity of the ALDH1 enzyme makes it possible to remove the chemotherapy-resistant or antiandrogen-resistant nature induced by ALDH1.

There are, within a cancer tumour, certain cancer cells known as multi-drug resistant (MDR) cells which have a resistant nature to chemotherapeutic agents. Among these, the R7 cells which overexpress the MDR gene have been disclosed as being resistant to daunorubicin [Jeannesson, P. et al., Cancer Res., 50, 1231-1236, (1990)].

The LY-ar cell line, of mouse lymphoma cells, has been disclosed as being resistant to radiation, unlike the LY-as cells which are sensitive to radiotherapy [Mirkovic, N. et al., Oncogene, 15, 1461-1470, (1997)]. This resistance is due to an overexpression of the $bcl_2$ gene.

These compounds also have the advantage of inducing apoptosis in a large variety of transformed cells, thus allowing them to be used in the preparation of pharmaceutical compositions for treating a large number of cancer pathologies, and also other diseases, more particularly diseases associated with cell hyperproliferation, such as auto-immune diseases or allergies.

Although selectively inducing apoptosis in transformed cells, these compounds also show, in certain higher ranges of concentrations, apoptosis-inducing properties in normal cells, such as MRC5 cells. This allows them to be used in the preparation of cosmetic compositions intended in particular for preventing or treating chronological or light-induced ageing.

The subject-matter of the present invention also relates to the compounds of formula (I) above as medicinal products. The compounds according to the invention are particularly suitable in the following fields of treatment:

1) in the treatment or prevention of cancerous or precancerous conditions, 2) for treating dermatological complaints associated with a keratinization disorder relating to differentiation and to proliferation, in particular for treating common acne, comedones, polymorphs, rosacea, nodulokystic acne, acne conglobata, senile acne and secondary acne such as solar, medicinal or occupational acne, 3) for treating ichthyosis, ichthyosiform conditions, palmoplantar keratoderma, leukoplakia and leukoplakiform conditions, 4) for treating dermatological complaints with an inflammatory immuno-allergic component, with or without a cellular proliferation disorder, and in particular all forms of psoriasis, whether cutaneous, mucous or ungual psoriasis, and even arthropathia psoriatica, or alternatively cutaneous atopy such as eczema, or respiratory atopy or gingival hypertrophy, 5) for treating dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and prickle cell epithelioma, and also precancerous skin lesions such as keratoacanthomas, 6) for treating immune dermatitides such as lupus erythematosus, bullous immune diseases and collagen diseases, such scleroderma, 7) in the treatment of dermatological or systemic complaints with an immunological component, 8) for combating sebaceous function disorders such as the hyperseborrhea of acne or simple seborrhea, 9) in the treatment of skin disorders due to exposure to UV radiation, and also for repairing or combating ageing of the skin, whether light-induced or chronological ageing, or for reducing actinic keratoses and pigmentations, or any pathology associated with chronological or actinic ageing, 10) for preventing or treating cicatrization disorders or for preventing or repairing stretch marks, 11) in the treatment of inflammatory complaints such as arthritis, 12) in the treatment of any cutaneous or systemic complaint of viral origin, such as Kaposi's syndrome or hepatitis, and 13) for treating certain ophthalmological disorders, in particular corneopathy.

In the therapeutic fields mentioned above, the compounds according to the invention may be advantageously used in combination with 3-methylthio-propanoyl thioester compounds of thioctic acid, methional, numerous antineoplastic agents, retinoids, with corticosteroids or oestrogens, in combination with antioxidants, with α-hydroxy acids or α-ceto acids or derivatives thereof, with potassium-channel blockers, in combination with other medicinal products known to interfere with the immune system (for example cyclosporin, FK 506, glucocorticoids, monoclonal antibodies, cytokines or growth factors), in combination with vitamin D derivatives or with vitamin D analogue compounds.

Among the antineoplastic agents which may be mentioned in particular are dexamethasone, cyclophosphamide, cisplatin, etoposide and BCNU (N,N-bis(2-chloroethyl)-N-nitrosourea), which are also capable of inducing apoptosis.

Among the 3-methylthiopropanoyl thioesters of thioctic acid which may be mentioned in particular are the compounds disclosed in patent application EP 947 503 and more particularly compound 21, that is to say 2'-(trimethylammonium)ethyl 6S,8S-bis(3-methyl-thiopropanoyl)octanoate iodide referred to hereinbelow as Metmetlico.

Specifically, a synergistic effect of the compounds of the invention has been revealed in their antitumour activity when they are used in combination with an antitumour therapeutic agent as disclosed in patent application EP 947 503.

The term "retinoid" means RAR or RXR receptor ligands, of natural or synthetic, agonist or antagonist type.

Among the D vitamins or derivatives thereof which may be mentioned in particular are vitamin $D_2$ and $D_3$ derivatives and in particular 1,25-dihydroxy-vitamin D3, and compounds that are vitamin D analogues chosen from the compounds disclosed in patent applications FR 98/13747, FR 99/14783 or FR 99/14781.

Among the antioxidants which may be mentioned in particular are α-tocopherol, superoxide dismutase, ubiquinol and certain metal-chelating agents.

Among the α-hydroxy acids or α-ceto acids or derivatives thereof which may be mentioned in particular are ketoleucine, ketoisoleucine, ketovaline, 2-oxobutyrate, 4-methylthio-2-oxobutanoic acid, lactic acid, malic acid, citric acid, glycolic acid, mandelic acid, tartaric acid and glyceric acid or salts, amides or esters thereof.

Among the potassium-channel blockers which may be mentioned in particular are minoxidil (2,4-diamino-6-piperidinopyrimidine 3-oxide) and its derivatives.

The Applicant has also found, surprisingly and unexpectedly, synergistic activity due to the combination of two compounds according to the invention.

A subject of the present invention is also novel pharmaceutical or cosmetic compositions containing, as active principle, an effective amount of at least one novel compound which is the subject of the invention, in a physiologically acceptable excipient.

A subject of the present invention is thus also such a pharmaceutical composition intended in particular for treating the abovementioned complaints.

The present invention also relates to novel pharmaceutical compositions for the treatment, regression and prevention of cancer, containing, as antitumour therapeutic agent, an effective amount of at least one novel compound which is the subject of the present invention, alone or in combination with an antitumour therapeutic agent chosen from those disclosed in patent application EP 947 503.

The compounds according to the invention may be administered enterally, parenterally, topically or ocularly.

Via the enteral route, the pharmaceutical compositions may be in the form of tablets, gel capsules, sugar-coated tablets, syrups, suspensions, solutions, powders, granules, emulsions, or lipid or polymer vesicles or nanospheres or microspheres to allow controlled release.

Via the parenteral route, the composition may be in the form of solutions or suspensions for infusion or for injection.

The compounds of formula (I) according to the invention are generally administered at a daily dose of about 0.001 mg/kg to 100 mg/kg of bodyweight in 1 to 3 dosage intakes.

Via the topical route, the cosmetic or pharmaceutical composition based on compounds according to the invention is more particularly intended for treating the skin of the scalp and mucous membranes and may be in the form of ointments, creams, milks, pommades, powders, impregnated pads, solutions, gels, sprays, lotions or suspensions. It may also be in the form of lipid or polymer vesicles or nanospheres or microspheres or polymer patches or hydrogels to allow controlled release. As a variant, it may be in the form of a shampoo, a conditioner or a soap.

These topical-route compositions may be in anhydrous form, in aqueous form or in the form of an emulsion depending on the therapeutic indication.

Via the ocular route, they are mainly eye drops.

For a pharmaceutical application, the compounds of formula (I) are used topically or ocularly at a concentration generally of between 0.0001% and 10% by weight and preferably between 0.001% and 1% by weight relative to the total weight of the composition.

The compounds of formula (I) according to the invention also find an application in the cosmetic field, in particular in hair and body hygiene and especially for the treatment of skin with a tendency towards acne, for the treatment or the prevention of stretch marks, in protecting against harmful effects of sunlight, for preventing or combating light-induced or chronological ageing, or for combating the greasy appearance of the skin or the hair.

The concentration of compound of formula (I) in cosmetic compositions may be between 0.001% and 3% by weight relative to the total weight of the composition.

The pharmaceutical or cosmetic compositions according to the invention may also contain inert or even pharmacodynamically or cosmetically active additives or combinations of these additives, and in particular: wetting agents; depigmenting agents such as hydroquinone, azeleic acid, caffeic acid or kojic acid; emollients; moisturizers such as glycerol, PEG-400, thiamorpholinone and its derivatives or urea; antiseborrhic or anti-acne agents, such as S-carboxymethylcysteine, S-benzylcysteamine, their salts and their derivatives, or benzoyl peroxide; antibiotics such as erythromycin and its esters, neomycin, clindamycin and its esters, and tetracyclines; antifungal agents such as ketoconazole or poly(4,5-methylene-3-isothiazolinones); agents for promoting hair regrowth, such as minoxidil (2,4-diamino-6-piperidino-pyrimidine 3-oxide) and its derivatives, diazoxide (7-chloro-3-methyl-1,2,4-benzo-thiadiazine 1,1-dioxide) and phenyloin (5,4-diphenyl-imidazoline-2,4-dione); non-steroidal anti-inflammatory agents; carotenoids and in particular β-carotene; anti-psoriatic agents such as anthralin and its derivatives, and, finally, eicosa-5,8,11,14-tetraynoic acid and eicosa-5,8,11-triynoic acid, and their esters and amides.

The compositions according to the invention may also contain flavour enhancers, preserving agents such as para-hydroxybenzoic acid esters, stabilizers, moisture regulators, pH regulators, osmotic pressure modifiers, emulsifiers or UV-A and UV-B screening agents.

Needless to say, a person skilled in the art will take care to select the optional compound(s) to be added to these compositions such that the advantageous properties intrinsically associated with the present invention are not, or are not substantially, adversely affected by the addition envisaged.

Several examples of the production of active compounds of formula (I) according to the invention and examples of tests to evaluate the biological activity of the compounds of formula (I) according to the invention will now be given by way of illustration and with no limiting nature.

A. EXAMPLES OF COMPOUNDS

Example 1

Process for the Preparation of S-methyl 4-dimethyl-amino-4-methyl-2-pentynethioate 4.07 ml (9.24 mmol) of a 2.27 M solution of n-butyllithium in hexane is added over 5 minutes at −70° C. to a solution of 0.855 g of 3-dimethylamino-3-methyl-1-butyne [Hennion, G. F., Nelson, K. W. (1957) J. Am. Chem. Soc., 79, 2142-2144]. After 5 minutes, the reaction medium is warmed to 0° C. and stirred for a further 30 minutes at this temperature. After cooling to −70° C., 2 ml of precondensed carbon oxysulphide are cannulated in and the mixture is stirred for 30 minutes at −70° C. The reaction medium is then maintained at 0° C. for 30 minutes, followed by addition of 0.575 ml (9.24 mmol) of methyl iodide and stirring is continued for 2 hours at 0° C. The resulting mixture is diluted in 250 ml of ether, washed with saturated sodium chloride solution (3×30 ml) and dried over sodium sulphate. After evaporation under vacuum and purification by chromatography on silica gel (eluting with a 70/30 petroleum ethyl/ethyl acetate mixture), 1.16 g of the compound of Example 1 are isolated in the form of a colourless oil (yield: 81%).

$^1$H NMR (300 MHz, CDCl$_3$): ν=1.42 (s, 6H, (CH$_3$)$_2$C), 2.31 (s, 6H, (CH$_3$)$_2$N), 2.39 (s, 3H, CH$_3$S).

Example 2

Process for the Preparation of S-methyl 4-methyl-4-trimethylammonium-2-pentynethioate iodide 0.25 ml (4.02 mmol) of methyl iodide is added to 0.184 g (0.99 mmol) of the compound obtained in Example 1 in 10 ml of ethyl acetate at room temperature. The mixture is stirred for 4 days in the dark. The resulting mixture is evaporated under vacuum and the residue is purified by chromatography on silica gel (eluting with a 90/10 dichloromethane/methanol mixture). 0.229 g of the compound of Example 2 (70% yield) is thus isolated in the form of a solid.

$^1$H NMR (300 MHz, CDCl$_3$): ν=1.96 (s, 6H, (CH$_3$)$_2$C), 2.46 (s, 3H, CH$_3$S), 3.62 (s, 6H, (CH$_3$)$_3$N).

Example 3

Process for the Preparation of S-methyl 4-di-n-propylamino-4-methyl-2-pentynethioate Preparation identical to that described in Example 1, using 3-di-n-propylamino-3-methyl-1-butyne [Hennion, G. F., Hanzel, R. F., J. Am. Chem. Soc., 82, 4908-4912, (1960)] instead of 3-dimethylamino-3-methyl-1-butyne. Scale: 2.8 mmol, purification by chromatography on silica gel (eluent: 95/5 petroleum ether/ethyl acetate), yield: 75%. Colourless oil.

$^1$H NMR (300 MHz, CDCl$_3$): ν=0.86 (t, J=7.36, 6H, CH$_3$—CH$_2$) 1.46 (s, 6H, (CH$_3$)$_2$C), 1.47 (m, 4H, CH$_3$—CH$_2$) 2.38 (s, 3H, CH$_3$S), 2.52 (m, 4H, CH$_2$N).

Example 4

Process for the Preparation of S-methyl 4-methyl-4-pyrrodin-1-yl-2-pentynethioate Preparation identical to that described in Example 1, using 3-methyl-3-pyrrodin-1-yl-1-butyne [Hennion, G. F., Nelson, K. W., J. Am. Chem. Soc., 79, 2142-2144, (1957)] instead of 3-dimethylamino-3-methyl-1-butyne. Scale: 2.8 mmol, purification by chromatography on silica gel (eluent: 70/30 petroleum ether/ethyl acetate), yield: 85%. Colourless oil.

$^1$H NMR (300 MHz, CDCl$_3$): ν=1.45 (s, 6H, (CH$_3$)$_2$C), 1.81 (m, 4H, NCH$_2$—CH$_2$), 2.39 (s, 3H, CH$_3$S), 2.72 (m, 4H, CH$_2$N).

Example 5

Process for the Preparation of S-methyl 4-methyl-4-morpholin-4-yl-2-pentynethioate Preparation identical to that described in Example 1, using 3-di-n-propylamino-3-methyl-1-butyne [Hennion, G. F., Hanzel, R. F., J. Am. Chem. Soc., 82, 4908-4912, (1960)] instead of 3-methyl-3-morpholin-4-yl-1-butyne. Scale: 1.5 mmol, purification by chromatography on silica gel (eluent: 60/40 petroleum ether/ethyl acetate), yield: 77%. White solid.

$^1$H NMR (300 MHz, CDCl$_3$): ν=1.43 (s, 6H, (CH$_3$)$_2$C), 2.40 (s, 3H, CH$_3$S), 2.65 (m, 4H, CH$_2$O), 3.97 (m, 4H, CH$_2$N).

B. EXAMPLES OF TESTS TO EVALUATE THE BIOLOGICAL ACTIVITY OF THE COMPOUNDS OF THE INVENTION

Example 1

Effect of the Compounds on the Growth of Transformed or Untransformed Cells a) Effect of the Compounds on the Growth of DU145 and BAF3 bcl$_2$ Cells The cells used correspond to two cell lines: metastatic cells of human prostate cancer (DU145) and murine lymphoid cells transfected with the human bcl$_2$ gene (BAF3 bcl$_2$).

The procedure used for the tests on DU145 is as follows:
10$^5$ cells are incubated in the various wells of a microplate in 1 ml of culture medium.

The compounds are added 4 hours after placing the cells in the wells.

After 72 hours, the cells are removed at different times. The DU145 cells are washed twice with PBS and recovered directly with 0.1M sodium chloride.

The effect on the growth of the DU145 cells is measured by protein assay according to the Lowry method (Lowry, O. H., Rosenbrough, N. J., Farr, A. L. and Randall, J. Biol. Chem. 193, 265-275, (1951)) and DNA assay by the Hoechst method (West, D. C., Sattar, A. and Kumar, S., Anal. Biochem. 147, 289-295, (1985)).

The procedure used for the tests on BAF3 bcl$_2$ cells is as follows:
10$^5$ cells are incubated in the various wells of a microplate in 1 ml of culture medium. After incubation for 4 hours, the test compounds are added to the wells containing the BAF3 bcl$_2$ cells.

For the BAF3 bcl$_2$ cells, the growth is measured by counting the viable cells in the presence of 0.1% Trypan blue. The control consists of thioampal, disclosed in patent application WO 98/44919.

The results are collated in Table 1 below:

TABLE I

|  |  | IC50 (μM) | |
| --- | --- | --- | --- |
|  |  | DU145 | BAF3 bcl$_2$ |
| Comparative example | Thioampal | 650 | 100 |
| Compounds of the invention | Example 1 | 5.9 | 0.25 |
|  | Example 3 | 8 | 2.7 |
|  | Example 4 | 7.2 | 2.7 |
|  | Example 5 | 8.8 | 12.0 |

The IC$_{50}$ concentration is the concentration corresponding to a 50% inhibition of cell growth.

These results show that the IC$_{50}$ values of the compounds of the invention are very much lower than that obtained for thioampal. Thus, the inhibition of growth of the DU145 cells and of the BAF3 bcl$_2$ cells obtained with the compounds according to the invention is greater than the inhibition obtained with thioampal.

This inhibition of the growth of DU145 cells and of BAF3 bcl$_2$ cells is at least partly due to an increase in the phenomena of apoptosis of these cells.

Thus, these results suggest that the compounds of the invention induce apoptosis in the DU145 cells and in the BAF3 bcl$_2$ cells more than thioampal.

b) Effect of the Compounds on the Growth of L1210, L1210T, B16 and MRC5 Cells

The cells used correspond to various cell lines: human lung normal embryonic fibroblasts (MRC5), mouse melanoma cells (B16), mouse lymphocytic leukaemia cells (L1210) and L1210T cells obtained by infecting L1210 cells with a retroviral vector bearing human ALDH1 cDNA.

The procedure used for the tests on the L1210 cells is as follows:

$10^5$ cells are incubated in the various wells of a microplate in 1 ml of culture medium. After incubating for 4 hours, the test compounds are added to the wells containing the L1210 cells.

For the L1210 cells, the growth is measured by counting the viable cells in the presence of 0.1% Trypan blue.

The procedure used for the tests on the B16 and MRC5 cells is as follows:

The test compounds are added 4 hours after placing the cells in the wells. After 72 hours, the cells are removed at different times. The B16 and MRC5 cells are washed twice with PBS and recovered directly with 0.1M sodium chloride.

The effect on the growth of the B16 and MRC5 cells is measured by protein assay according to the Lowry method (Lowry, O. H., Rosenbrough, N. J., Farr, A. L. and Randall, J. Biol. Chem. 193, 265-275, (1951)) and DNA assay by the Hoechst method (West, D. C., Sattar, A. and Kumar, S., Anal. Biochem. 147, 289-295, (1985)).

The results are collated in Table II below:

TABLE II

|  |  | IC50 (μM) | | | |
| --- | --- | --- | --- | --- | --- |
|  |  | L1210 | L1210T | B16 | MRC5 |
| Comparative example | Thioampal | 90 | 140 | NT | >600 |
| Compound of the invention | Example 1 | 1.2 | 1.6 | 0.8 | 8.4 |

NT means not tested

The IC$_{50}$ concentration is the concentration corresponding to a 50% inhibition of growth of the cells.

These results show that the IC$_{50}$ values of the compounds of the invention are very low and very much lower than those obtained for thioampal. Thus, the inhibition of growth of the L1210, L1210T, B16 and MRC5 cells which is obtained with the compounds according to the invention is significant and is much stronger than the inhibition obtained with thioampal.

This inhibition of growth of the L1210, L1210T, B16 and MRC5 cells is at least partly due to an increase in the phenomena of apoptosis of these cells. Thus, these results suggest that the compounds of the invention induce apoptosis in the L1210, L1210T, B16 and MRC5 cells more than thioampal.

2—Measurement of Apoptosis Induction in BAF3-b0 and BAF3-bcl$_2$ Cells with the Compounds of the Invention The BAF3-bcl$_2$ cells correspond to BAF3 cells (mouse lymphocyte cells) tranfected with the bcl$_2$ gene. Among these cells, four lines known as H16, G18, B14 and G21 overexpress the bcl$_2$ gene.

Hereinbelow, the cells known as BAF3-b0 correspond to BAF3 cells not transfected with the bcl$_2$ gene.

Whereas the BAF3-b0 cells undergo apoptosis (more than 80% of the cells) in the absence of interleukin 3 (IL3) in 16 hours [according to Collins, M. K. L., Marvel, J., Malde, P. & Lopez-Rivas, A., J. Exp. Med. 176, 1043-1051, (1992)], the BAF3-bcl$_2$ cells show no sign of apoptosis in the absence of IL3. They are thus apoptosis-resistant.

The procedure which was used is as follows:

The BAF3-b0 or BAF3-bcl$_2$ cells, cultured in the presence of IL3, were labelled by a method adapted from that disclosed in Wright, S. et al., J. of Cell. Biochem. 48, 344-355, (1992).

$10^5$ cells/ml were incubated with 4.62 KBq.ml$^{-1}$ [$^3$H]-thymidine for 40 hours at 37° C. After two washes with culture medium, $2.5 \times 10^6$ cells were cultured in the presence of the test compound.

After incubating for 24 hours, these cells were recovered by centrifugation at 400×g for 5 minutes and washed 3 times with PBS buffer. The cells recovered in the pellet were lysed in 2 ml of 0.1% Triton X-100, 20 mM EDTA, 5 mM Tris pH 8 and centrifuged at 30 000×g at 4° C. for 30 minutes.

The supernatants were recovered and the pellets dissolved in 0.3 ml of 0.5N NaOH.

Aliquots of the culture medium (1 ml), of the supernatant (0.3 ml) and of the dissolved pellet (0.1 ml) were assayed in a scintillation counter.

The percentage of DNA fragments is calculated in the following way:

$$\% \text{ of DNA fragments} = \frac{dpm \text{ of the culture medium} + dpn \text{ of the supernatant}}{dpm \text{ of the culture medium} + dpm \text{ of the supernatant} + dpm \text{ of the dissolved pellet}}$$

($dpm$ = disintegrations per minute)

The percentage of fragmentation of the DNA is a direct measure of the apoptosis which the cells have undergone.

The results obtained are given in Table III

TABLE III

|  | Example 1 (μM) | b0 | bcl$_2$ Clones | | | |
|---|---|---|---|---|---|---|
|  |  |  | G21 | G18 | B14 | H16 |
| % expression of bcl$_2$ in BAF3 cells | 0 | 0 | 6.4 | 22.1 | 50.8 | 72 |
| DNA fragmentation (%) | 1 | 5.0 | 0 | 0.6 | 0 | 2.9 |
|  | 2 | 10.6 | 5.8 | 7.3 | 2.0 | 6.3 |
|  | 4 | 46.4 | 29.3 | 52.7 | 44.1 | 65.3 |
|  | 8 | 71.1 | 71.8 | 84.3 | 90.0 | 94.2 |

The BAF3-b0 cells serve as controls. The apoptosis of these cells is induced by adding the compound of Example 1, and this phenomenon increases in a dose-dependent manner.

These results show that the presence of a compound according to the invention makes it possible to remove the inhibition of apoptosis due to the bcl$_2$ gene in the H16, G18, B14 and G21 cell lines which overexpress the bcl$_2$ gene.

The procedure for the test given in Table 4 below is identical to the previous procedure except that the incubation time is 6 hours instead of 24 hours:

TABLE IV

| Concentration (μM) | % fragmentation of the DNA of the bcl$_2$ H16 cells | |
|---|---|---|
|  | Thioampal | Example 1 |
| 50 | 0 | 2.15 |
| 100 | 1.6 | 0 |
| 200 | 7.6 | 30.4 |
| 400 | 16.4 | 83.8 |
| 600 | 26.5 | 81.5 |

The apoptosis of these cells is induced much more strongly with the compound of Example 1 than with thioampal, and in a dose-dependent manner.

These results show that the presence of the compound according to the invention makes it possible to remove the inhibition of apoptosis due to the bcl$_2$ gene, and does so much more strongly than the compounds of the prior art.

Example 2

Effect of the Compounds on the Activity of ALDH1

The procedure used is given below: 260 mU of ALDH from baker's yeast are preincubated at 37 or 0° C. in a mixture of 1 mM EDTA, 100 mM KCl, in 60 mM of sodium phosphate buffer pH 6 in a final volume of 200 μl.

To each tube containing the 200 μl of mixture, the test compound is added to a concentration of 400 μM, with the exception of a control series which contains no test compound.

The incubation carried out at 0° C. or at 37° C. is stopped by adding 100 μg of BSA (bovine serum albumin) and acetone at −20° C. to a final concentration of 80% in order to precipitate the proteins (ALDH and BSA). The tubes are left at −20° C. for 1 hour and then centrifuged at 10 000 rpm for 10 minutes and washed with 80% acetone.

The proteins precipitated are dissolved in 358 μl of water and added immediately to the reaction complex consisting of 1 mM EDTA, 100 mM KCl and 2.35 mM NAD in 60 mM of pH 8.5 sodium phosphate buffer.

The reaction is started by adding 2 mM of propanal and the optical density (OD) is measured at 340 nm at T=0 and at T=5, 10, 20 and 30 minutes.

The activity of the enzyme is measured by the variation in optical density Δ OD per minute (Quash G. et al., *Enzymology and molecular biology of carbonyl metabolism*, Weiner et al. eds., Kluwer Academic/Plenum Publishers, New York, 97-106).

Figure 6:
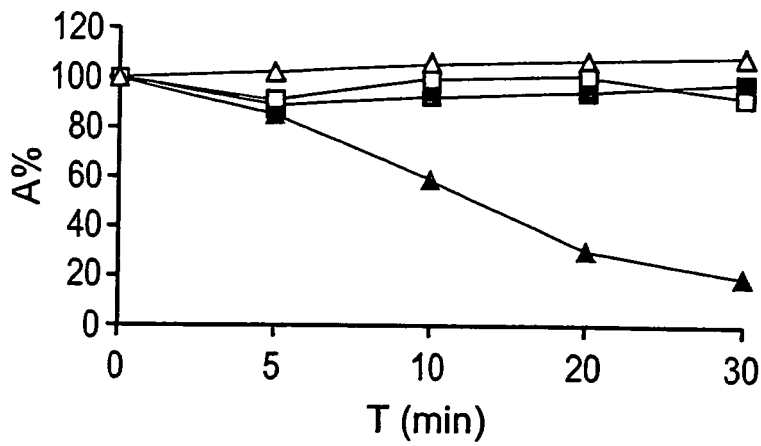
FIG. 6 is a graph of the percentage activity (A %) of the ALDH1 enzyme obtained at different preincubation times with the compound of Example 1 at 0° C. (■) or 37° C. (▲), or without preincubation with the compound of Example 1 at 0° C. (□) or at 37° C. (Δ), as a function of the time t in minutes.

The results obtained are given in FIG. 6.

The percentage activity (A %) of the ALDH1 enzyme obtained at different preincubation times with the compound of Example 1 at 0° C. (represented by ■) or 37° C. (represented by ▲) or alternatively without preincubation with the compound of Example 1 at 0° C. (represented by □) or at 37° C. (represented by Δ) is measured as a function of the time t (expressed in minutes).

When the pre-incubation with the compound of Example 1 is carried out at a temperature of 0° C., there is no effect of inhibition of the compound of Example 1 on the activity of the enzyme. Specifically, the two curves obtained with or without pre-incubation with the compound of Example 1 are superimposable. This is explained by the fact that, at this temperature, the compound of Example 1 has not been able to be metabolized by the ALDH1. Consequently, the formation of covalent bonds between the active principle formed after cleavage and the enzyme has not been able to be established.

On the other hand, when the pre-incubation with the compound of Example 1 is carried out at a temperature of 37° C., the enzyme ALDH1 metabolizes the compound of Example 1 and bonds to it via covalent bonds, and an effect of inhibition of the activity of the enzyme is observed. This effect increases as a function of the pre-incubation time with the compound of Example 1.

These results show that the compounds according to the invention make it possible to reduce the activity of ALDH, and have the advantage of being of "suicide" type (irreversible covalent bonding with the enzyme ALDH), thus making it possible to remove the resistance to anticancer agents.

Example 3

Effect of the Compounds on R7 Cells which Overexpress the MDR Gene

The K562 cells used in this test do not overexpress the MDR gene and serve as control, and are human myeloid leukaemia cells, in contrast with the R7 cells, cancer cells which overexpress the MDR gene.

The object of the present test is to demonstrate the effect of the compounds of the invention on these R7 cells.

The procedure used is given below:

$10^5$ cells were incubated in the various wells of a microplate in 1 ml of culture medium. These are R7 cells, on the one hand, and K562 cells, on the other hand.

After incubating for 4 hours, the test compound (compound of Example 1 according to the invention, on the one hand, and daunorubicin, on the other hand) was added to the wells containing the cells.

After 72 hours, the cells were collected at different times.

The growth of the cells was measured by counting the viable cells in the presence of 0.1% Trypan blue.

Figure 7:
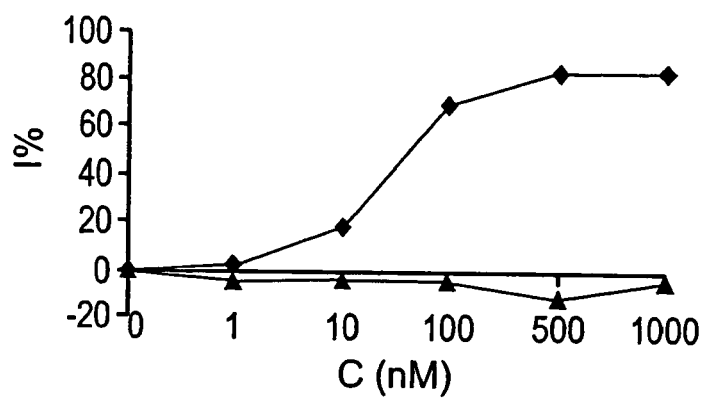
FIG. 7 is a graph representing the percentage inhibition (I %) by daunorubicin on the growth of R7(▲) cells and K562 (♦) cells obtained at increasing concentrations C.
Figure 8:
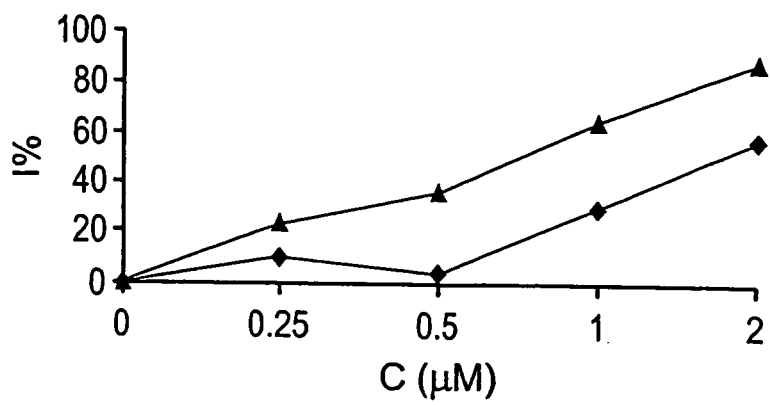
FIG. 8 is a graph representing the percentage inhibition (I %) by the compound of Example 1 on the growth of R7(▲) cells and K562(♦) cells obtained at increasing concentrations C.

The results are given in FIGS. 7 and 8.

FIGS. 7 and 8 respectively represent the percentage inhibition (I %) by daunorubicin and the compound of Example 1 on the growth of the R7 and K562 cells, obtained at increasing concentrations C. The results obtained with the K562 cells are symbolized by ♦ and those obtained with the R7 cells are symbolized by ▲.

These results show that daunorubicin has no inhibitory effect on the growth of the R7 cells overexpressing the MDR gene at concentrations at which it inhibits the growth of the K562 cells.

On the other hand, the compound of Example 1 very strongly inhibits the growth of the R7 cells. The inhibitory effect on the growth of the R7 cells is even greater than the inhibitory effect obtained at the same concentrations on the growth of the K562 cells.

These results show that the compounds according to the invention make it possible to remove the chemotherapy resistance due to the MDR gene.

Example 4

Effect of the Combination of a Compound According to the Invention and of a Compound Chosen from those Disclosed in Patent Application EP 947 503 on the Growth of DU145 Cells Patent application EP 947 503 discloses that methional derivatives comprising the methional coupled via a thioester bond to thioctic acid show strong selective apoptotic activity towards transformed cells and tumour cells. Among these compounds, mention may be made of 2'-(trimethylammonium)ethyl 6S,8S-bis(3-methyl-thiopropanoyl)octanoate iodide (compound 21 of this document) referred to as metmetlico.

The procedure used is given below:

The cells used correspond to metastatic cells of human prostate cancer DU145.

$10^5$ DU145 cells are incubated in the various wells of a microplate in 1 ml of culture medium.

The test compounds are added 4 hours after placing the cells in the wells. After 72 hours, the cells are removed at different times. The cells are washed twice with PBS and recovered directly with 0.1M sodium chloride.

The effect on the growth of DU145 cells is measured by protein assay according to the Lowry method (Lowry, O. H., Rosenbrough, N. J., Farr, A. L. and Randall, J. Biol. Chem. 193, 265-275, (1951)) and DNA assay by the Hoechst method (West, D. C., Sattar, A. and Kumar, S., Anal. Biochem. 147, 289-295, (1985)).

The test compounds are the compound of Example 1, metmetlico and a mixture thereof.

The results are collated in Table V.

TABLE V

| Compound (concentration) | % Inhibition of growth of the DU145 cells |
|---|---|
| Example 1 (2 μM) | 5.8 |
| Example 1 (3 μM) | 16.1 |

TABLE V-continued

| Compound (concentration) | % Inhibition of growth of the DU145 cells |
|---|---|
| Example 1 (4 μM) | 22.4 |
| Metmetlico (25 μM) | 0 |
| Metmetlico (50 μM) | 0 |
| Example 1 (2 μM) + Metmetlico (25 μM) | 14.7 |
| Example 1 (2 μM) + Metmetlico (50 μM) | 20.7 |
| Example 1 (3 μM) + Metmetlico (25 μM) | 26.9 |
| Example 1 (3 μM) + Metmetlico (50 μM) | 36.9 |
| Example 1 (4 μM) + Metmetlico (25 μM) | 44.4 |
| Example 1 (4 μM) + Metmetlico (50 μM) | 41.3 |

The results show that the compound of Example 1 alone inhibits the growth of the DU145 cells. On the other hand, Metmetlico alone has no inhibitory effect on the growth of these DU145 cells at the concentrations used in this example.

The combination of a compound according to the invention and of a compound disclosed in patent application EP 947 503 synergistically inhibits the growth of the DU145 cells. These results demonstrate the possibility of using these compounds in combination at doses that are very much lower than those which may be used when they are used alone.

Example 5

Effect of the Combination of Two Compounds According to the Invention on the Growth of DU145 Cells or Normal Cells $10^5$ normal human prostate cells or $10^5$ cancerous human prostate cells (DU145) are incubated in various wells of a microplate in 1 ml of culture medium.

The compounds are added 4 hours after placing the cells in the wells.

After 72 hours, the cells are removed at different times. The DU145 cells or the normal cells are washed twice with PBS and recovered directly with 0.1M sodium chloride.

The effect on the growth of the DU145 cells or the normal cells is measured by protein assay according to the Lowry method (Lowry, O. H., Rosenbrough, N. J., Farr, A. L. and Randall, J. Biol. Chem. 193, 265-275, (1951)) and DNA assay by the Hoechst method (West, D. C., Sattar, A. and Kumar, S., Anal. Biochem. 147, 289-295, (1985)).

TABLE VI

| Test product (concentration) | % Inhibition of normal human prostate cells | % Inhibition of DU145 cells |
|---|---|---|
| Example 1 (2 μM) | 3.7 | 21.3 |
| Example 5 (2 μM) | 1.3 | 25.2 |
| Example 5 (1 μM) | 0 | 14.3 |
| Example 1 (2 μM) + Example 5 (2 μM) | 6.1 | 67.7 |
| Example 1 (2 μM) + Example 5 (1 μM) | 2.8 | 53.8 |

The combination of two compounds according to the invention synergistically inhibits the growth of the cancer cells without any appreciable effect on the growth of the normal cells, thus making it possible to further increase the activity and selectivity of the compounds according to the invention with respect to transformed cells. These results demonstrate the possibility of using these compounds in combination at doses that are lower than those which may be used when the compounds are used alone.

C. FORMULATION EXAMPLES

1) Oral Route (a) The composition below is prepared in the form of a 0.2 g tablet

| | |
|---|---|
| Compound of Example 1 | 0.005 g |
| Pregelatinized starch | 0.065 g |
| Microcrystalline cellulose | 0.075 g |
| Lactose | 0.050 g |
| Magnesium stearate | 0.005 g |

(b) A drinkable suspension, intended to be packaged in 5 ml ampules, is prepared

| | |
|---|---|
| Compound of Example 2 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavouring qs | |
| Purified water qs | 5 ml |

(c) The formulation below intended to be packaged in gel capsules is prepared:

| | |
|---|---|
| Compound of Example 1 | 0.01 mg |
| Compound of Example 5 | 0.01 mg |
| Cyclosporin | 0.050 g |
| Corn starch | 0.060 g |
| Lactose qs | 0.300 g |

The gel capsules used consist of gelatin, titanium oxide and a preserving agent.

2) Topical Route (a) The nonionic water-in-oil cream below is prepared:

| | |
|---|---|
| Compound of Example 1 | 0.100 g |
| Mixture of emulsifying lanolin alchols, waxes and refined oils, sold by the company BDF under the name "anhydrous eucerin" | 39.900 g |
| Methyl para-hydroxybenzoate | 0.075 g |
| Propyl para-hydroxybenzoate | 0.075 g |
| Sterile demineralized water qs | 100.000 g |

(b) A gel is prepared by producing the following formulation:

| | |
|---|---|
| Compound of Example 1 | 0.001 g |
| Base erythromycin | 4.000 g |
| Butyl hydroxytoluene | 0.050 g |
| Hydroxypropylcelluluse sold by the company Hercules under the name "Klucel HF" | 2.000 g |
| Ethanol (at 95°) qs | 100.000 g |

(c) A lotion is prepared by mixing together the following ingredients:

| | |
|---|---|
| Compound of Example 2 | 0.030 g |
| Propylene glycol | 5.000 g |
| Butyl hydroxytoluene | 0.100 g |
| Ethanol (at 95°) qs | 100.000 g |

(d) A cosmetic composition to combat the harmful effects of sunlight is prepared by mixing together the following ingredients:

| | |
|---|---|
| Compound of Example 1 | 1.00 g |
| Benzylidenecamphor | 4.00 g |
| Fatty acid triglycerides | 31.00 g |
| Glyceryl monostearate | 6.00 g |
| Stearic acid | 2.00 g |
| Cetyl alcohol | 1.20 g |
| Lanolin | 4.00 g |
| Preserving agents | 0.30 g |
| Propylene glycol | 2.00 g |
| Triethanolamine | 0.50 g |
| Fragrance | 0.40 g |
| Demineralized water qs | 100.00 g |

(e) The nonionic oil-in-water cream below is prepared:

| | |
|---|---|
| Compound of Example 3 | 0.500 g |
| Retinoic acid | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

(f) A topical gel is prepared by mixing together the following ingredients:

| | |
|---|---|
| Compound of Example 4 | 0.050 g |
| Ethanol | 43.000 g |
| Tocopherol | 0.050 g |
| Carboxyvinyl polymer sold under the name "Carbopol 941" by the company "Goodrich" | 0.500 g |
| Triethanolamine as an aqueous solution at 20% by weight | 3.800 g |
| Water | 9.300 g |
| Propylene glycol qs | 100.000 g |

(g) An oil-in-water cream is prepared by producing the following formulation:

| | |
|---|---|
| Compound of Example 4 | 0.020 g |
| Betamethasone 17-valerate | 0.050 g |
| S-carboxymethylcysteine | 3.000 g |
| Polyoxyethylene stearate (40 mol of ethylene oxide), sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl monostearate and distearate sold under the name "Geleol" by the company "Gattefosse" | 4.200 g |
| Propylene glycol | 10.000 g |
| Butyl hydroxyanisole | 0.010 g |
| Butyl hydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water qs | 100.000 g |

(h) The oil-in-water type cream below is prepared:

| | |
|---|---|
| Lactic acid | 5.000 g |
| Compound of Example 2 | 0.020 g |
| Polyoxyethylene stearate (40 mol of ethylene oxide) sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl monostearate and distearate sold under the name "Geleol" by the company "Gattefosse" | 4.200 g |
| Propylene glycol | 10.000 g |
| Butyl hydroxyanisole | 0.010 g |
| Butyl hydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Water qs | 100.000 g |

-continued (i) The anhyrous ointment below is prepared:

| | |
|---|---|
| Compound of Example 1 | 5.00 g |
| Liquid petroleum jelly | 50.00 g |
| Butyl hydroxytoluene | 0.05 g |
| White petroleum jelly qs | 100.00 g |

3) Intralesional Route (a) The composition below is prepared:

| | |
|---|---|
| Compound of Example 3 | 0.002 g |
| Ethyl oleate qs | 10 g |

(b) The composition below is prepared:

| | |
|---|---|
| Compound of Example 1 | 0.05% |
| Polyethylene glycol | 20% |
| 0.9% NaCl solution qs | 100 |

(c) The composition below is prepared:

| | |
|---|---|
| Compound of Example 3 | 2.5% |
| Polyethylene glycol 400 | 20% |
| 0.9% NaCl solution qs | 100 |

4) Intravenous Route (a) The injectable composition below is prepared:

| | |
|---|---|
| Compound of Example 1 | 0.001% |
| Metmetlico | 0.01% |
| Polyethylene glycol 400 | 20% |
| 0.9% NaCl solution qs | 100 |

(b) The injectable composition below is prepared:

| | |
|---|---|
| Compound of Example 2 | 0.01% |
| Polyethylene glycol 400 | 20% |
| 0.9% NaCl solution qs | 100 |

(c) The cyclodextrin composition below is prepared:

| | |
|---|---|
| Compound of Example 3 | 0.1 mg |
| Cyclodextrin | 0.10 g |
| Water for injection qs | 10.00 g |

(d) The cyclodextrin composition below is prepared:

| | |
|---|---|
| Compound of Example 4 | 0.01 g |
| 2-Hydroxypropylcyclodextrin | 0.10 g |
| Water for injection qs | 10.00 g |

What is claimed is:

1. A method for the treatment, regression, and/or hindering of further development of prostate cancer which is resistant to the induction of apoptosis, wherein said resistance is due to the presence in cancer cells of the $bcl_2$ gene, or the MDR gene, or the BCL-$X_L$ gene, or the enzyme ALDH, said method comprising administering to a subject in need of such treatment at least one compound selected from the group consisting of:
  S-methyl 4-dimethylamino-4-methyl-2-pentynethioate;
  S-methyl 4-di-n-propylamino-4-methyl-2-pentynethioate;
  S-methyl 4-methyl-4-pyrrolidin-1-yl-2-pentynethioate; and
  S-methyl 4-methyl-4-morpholin-4-yl-2-pentynethioate.

2. A method for the treatment, regression, and/or hindering of further development of prostate cancer which is resistant to the induction of apoptosis in cells due to the $bcl_2$ gene, or the MDR gene, or the BCL-$X_L$ gene, or the enzyme ALDH present in said cells, said method comprising administering to a subject in need of such treatment at least one compound selected from the group consisting of:
  S-methyl 4-dimethylamino-4-methyl-2-pentynethioate;
  S-methyl 4-d i-n-propylamino-4-methyl-2-pentynethioate;
  S-methyl 4-methyl-4-pyrrolidin-1-yl-2-pentynethioate; and
  S-methyl 4-methyl-4-morpholin-4-yl-2-pentynethioate;
wherein said at least one compound is administered in combination with at least one 3-methylthiopropanoyl thioester of thioctic acid.

3. The method according to claim 2, wherein said thioester of thioctic acid is 2'-(trimethylammonium)ethyl 6S, 8S-bis (3-methylthiopropanoyl)octanoate iodide.

4. The method according to claim 1, wherein said at least one compound is S-methyl 4-dimethylamino-4-methyl-2-pentynethioate or S-methyl 4-methyl-4-morpholin-4-yl-2-pentynethioate or a mixture thereof.

5. The method according to claim 1, wherein said at least one compound is S-methyl 4-methyl-4-morpholin-4-yl-2-pentynethioate.

6. The method according to claim 1, wherein the at least one compound administered is S-methyl 4-dimethylamino-4-methyl-2-pentynethioate or S-methyl 4-methyl-4-morpholin-4-yl-2-pentynethioate or a mixture thereof.

7. A method for the treatment, regression, and/or hindering of further development of prostate cancer which is resistant to the induction of apoptosis in cells due to the $bcl_2$ gene, or the MDR gene, or the BCL-$X_L$ gene, or the enzyme ALDH present in said cells, said method comprising administering to a subject in need of such treatment at least one compound selected from the group consisting of:
  S-methyl 4-di-n-propylamino-4-methyl-2-pentynethioate;
  S-methyl 4-methyl-4-pyrrolidin-1-yl-2-pentynethioate; and
  S-methyl 4-methyl-4-morpholin-4-yl-2-pentynethioate.

\* \* \* \* \*